United States Patent [19]

Gatti et al.

[11] Patent Number: 4,946,831
[45] Date of Patent: Aug. 7, 1990

[54] INJECTABLE READY-TO-USE SOLUTIONS CONTAINING AN ANTITUMOR ANTHRACYCLINE GLYCOSIDE

[75] Inventors: Gaetano Gatti; Diego Oldani, both of Milan; Giuseppe Bottoni, Bergamo; Carlo Confalonieri, Milan; Luciano Gambini, Milan; Roberto De Ponti, Milan, all of Italy

[73] Assignee: Farmitalia Carlo Erba S.p.A., Milan, Italy

[21] Appl. No.: 385,999

[22] Filed: Jul. 27, 1989

Related U.S. Application Data

[63] Continuation of Ser. No. 878,784, Jun. 26, 1986, abandoned.

[30] Foreign Application Priority Data

Aug. 2, 1985 [GB] United Kingdom ............... 8519452

[51] Int. Cl.$^5$ ............................................. A61K 31/70
[52] U.S. Cl. ........................................ 514/34; 536/6.4
[58] Field of Search ............................................. 514/34

[56] References Cited

U.S. PATENT DOCUMENTS

| | | | |
|---|---|---|---|
| 3,590,028 | 6/1971 | Arcamone et al. | 536/6.4 |
| 4,039,663 | 8/1977 | Arcamone et al. | 514/34 |
| 4,058,519 | 11/1977 | Arcamone et al. | 536/6.4 |
| 4,067,969 | 1/1978 | Penco et al. | 514/34 |
| 4,077,988 | 3/1978 | Arcamone et al. | 260/363 |
| 4,177,264 | 12/1979 | Wu et al. | 514/34 |
| 4,325,947 | 4/1982 | Penco et al. | 514/34 |
| 4,438,105 | 3/1984 | Suarato et al. | 514/34 |

FOREIGN PATENT DOCUMENTS

| | | |
|---|---|---|
| 2124224A | 2/1984 | United Kingdom . |
| 2200047A | 7/1988 | United Kingdom . |

OTHER PUBLICATIONS

Andrew G. Bosanquet, Stability of Solutions of Antineoplastic . . . , Cancer Chemother Pharmacol. (1986) 17:1–10.
F. Arcamone, et al., Structure and Physicochemical Properties . . . , International Symposium on Adriamycin (1972) 9–22.
J. H. Beijnen, et al, Stability of Antracycline Antitumour . . . , Research Article, vol. 39, No. 6, Nov.--Dec. (1985) 220–222.
Teresa Kaniewska, Badanie Rozkladu Adriamycyny, Farmacja Polsaka, XXXIII, 9, (1977), 539–542.
Guiragos K. Poochikian, et al., Stability of Anthracycline Antitumor Agents . . . , American Journal of Hospital Pharmacy, vol. 38, (Apr. 1981, 483–486.
J. H. Beijnen, et al., Aspects of the Chemical Stability . . . , Pharmaceutisch Weekblad Scientific Edition, vol. 7-1985, 109–116.
Dennis M. Hoffman, et al., Stability of Refrigerated and Frozen Solutions . . . , American Journal of Hospital Pharmacy, vol. 36(1979) 1536–1538.
Staffan Eksborg, et al., Liquid Chromatography in Anticancer Drug . . . , Journal of Pharmaceutical & Biomedical Analysis, vol. 2, no. 2, (184) 297–303.
T. Masuike, et al., Determination of Adriamycin and Its Metabolites . . . , YKKZAJ: J.Pharm.Soc.Jpn. vol. 104, no. 6, (1984), 614–23.
M. J. H. Janssen, et al., Doxorubicin Decomposition on Storage . . . International Journal of Pharmaceutics, 23 (1985) 1–11.
Aristide Vigevani and Martin J. Williamson, Doxorubicin, Analytical Profiles of Drug Substances, vol. 9, Academic Press (1980), pp. 244–274.
Karsten Wasserman and Hans Bundgaard, Kinetics of the Acid–Catalyzed Hydrolysis of Doxorubicin, International Journal of Pharmaceutics, 14 (1983) pp. 73–78.
Stability and Compatibility of Antitumor Agents in Glass and Plastic Containers, John A. Benvenuto, American Journal of Hospital Pharmacy, vol. 38.
Chemical Abstracts, vol. 104, No. 6, Feb. 10, 1986, p. 382 No. 39716d Columbus, Ohio & JP-A-60 92 212 (Kyowa Hakko Kogyo Co., Ltd.) 23-05-1985.
Int. J. of Pharmaceutics 31 (1986) 75–82, J. H. Beijnen et al.

*Primary Examiner*—Johnnie R. Brown
*Assistant Examiner*—Elli Peselev
*Attorney, Agent, or Firm*—Oblon, Spivak, McClelland, Maier & Neustadt

[57] ABSTRACT

According to the invention there is provided a sterile, pyrogen-free, ready-to-use solution of an anthracycline glycoside, especially doxorubicin, which consists essentially of a physiologically acceptable salt of an anthracycline glycoside dissolved in a physiologically acceptable solvent therefor, which has not been reconstituted from a lyophilizate and which has a pH of from 2.5 to 6.5. The solution of the invention is particularly advantageous for the administration by injection of the anthracycline glycoside drugs, e.g. doxorubicin, in the treatment of both human and animal tumors.

6 Claims, No Drawings

INJECTABLE READY-TO-USE SOLUTIONS CONTAINING AN ANTITUMOR ANTHRACYCLINE GLYCOSIDE

This application is a continuation of application Ser. No. 878,784, filed on June 26, 1986, now abandoned.

The present invention relates to a stable intravenously injectable ready-to-use solution of an antitumor anthracycline glycoside, e.g. doxorubicin, to a process for preparing such a solution, and provide the same in a sealed container, and to a method for treating tumors by the use of the said ready-to-use solution. The anthracycline glycoside compounds are a well known class of compounds in the antineoplastic group of agents, wherein doxorubicin is a typical, and the most widely used, representative: Doxorubicin. Anticancer Antibiotics, Federico Arcamone, 1981, Publ: Academic Press, New York, N.Y.; Adriamycin Review, EROTC International Symposium, Brussels, May, 1974, edited by M. Staquet, Publ. Eur. Press Medikon, Ghent, Belg.; Results of Adriamycin Therapy, Adriamycin Symposium at Frankfurt/Main 1974 edited by M. Ghione, J. Fetzer and H. Maier, publ.: Springer, New York, N.Y.

At present, anthracycline glycoside antitumor drugs, in particular, e.g., doxorubicin, are solely available in the form of lyophilized preparations, which need to be reconstituted before administration.

Both the manufacturing and the reconstitution of such preparations expose the involved personnel (workers, pharmacists, medical personnel, nurses) to risks of contamination which are particularly serious due to the toxicity of the antitumor substances.

The Martindale Extra Pharmacopoeia 28th edition, page 175 left column, reports, indeed, about adverse effects of antineoplastic drugs and recommends that "They must be handled with great care and contact with skin and eyes avoided; they should not be inhaled. Care must be taken to avoid extravasation since pain and tissue damage may ensue.".

Similarly, Scand. J. Work Environ Health vol.10 (2), pages 7174 (1984), as well as articles on Chemistry Industry, Issue July 4, 1983, page 488, and Drug-Topics-Medical-Economics-Co, Issue February 7, 1983, page 99 report about severe adverse effects observed in medical personnel exposed to use of cytostatic agents, including doxorubicin.

To administer a lyophilized preparation, double handling of the drug is required, the lyophilized cake having to be first reconstituted and then administered and, moreover, in some cases, the complete dissolution of the powder may require prolonged shaking because of solubilization problems.

As the risks connected with the manufacturing and the reconstitution of a lyophilized preparate would be highly reduced if a ready-to-use solution of the drug were available, we have developed a stable, therapeutically acceptable intravenously injectable solution of an anthracycline glycoside drug, e.g. doxorubicin, whose preparation and administration does not require either lyophilization or reconstitution.

According to the present invention, there is provided a sterile, pyrogen-free, anthracycline glycoside solution which consists essentially of a physiologically acceptable salt of an anthracycline glycoside dissolved in a physiologically acceptable solvent therefor, which has not been reconstituted from a lyophilizate and which has a pH of from 2.5 to 6.5.

Preferably the solution of the invention is provided in a sealed container.

Preferably the anthracycline glycoside is chosen from the group consisting of doxorubicin, 4'-epi-doxorubicin (i.e. epirubicin), 4'-desoxy-doxorubicin (i.e. esorubicin), 4'-desoxy-4'-iodo-doxorubicin, daunorubicin and 4-demethoxydaunorubicin (i.e. idarubicin).

A particularly preferred anthracycline glycoside is doxorubicin.

Any physiologically acceptable salt of the anthracycline glycoside may be used for preparing the solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutammic, benzoic, methanesulfonic, ethanesulfonic and the like. The salt with hydrochloric acid is a particularly preferred salt, especially when the anthracycline glycoside is doxorubicin.

Any solvent which is physiologically acceptable and which is able to dissolve the anthracycline glycoside salt may be used. The solution of the invention may also contain one or more additional components such as a co-solubilizing agent (which may be the same as a solvent), a tonicity adjustment agent and a preservative. Examples of solvents, co-solubilizing agents, tonicity adjustment agents and preservatives which can be used for the preparation of the anthracycline glycoside solutions of the invention are hereunder reported.

Suitable solvents and co-solubilizing agents may be, for instance, water; physiological saline; aliphatic amides, e.g. N,N-dimethylacetamide, N-hydroxy-2-ethyllactamide and the like; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols, e.g. Brij ® and the like; esters of polyoxyethylenated fatty acids, e.g. Cremophor ®, Myrj ® and the like; polysorbates, e.g. Tweens ®; polyoxyethylene derivatives of polypropyleneglycols, e.g. Pluronics ®.

A particularly preferred co-solubilizing agent is polyvinylpyrrolidone.

Suitable tonicity adjustment agents may be, for instance, physiologically acceptable inorganic chlorides, e.g. sodium chloride, dextrose, lactose, mannitol and the like.

Preservatives suitable for physiological administration may be, for instance, esters of para-hydroxybenzoic acid (e.g., methyl, ethyl, propyl and butyl esters, or mixtures of them), chlorocresol and the like.

The above mentioned solvents and co-solubilizing agents, tonicity adjustment agents and preservatives can be used alone or as a mixture of two or more of them.

Examples of preferred solvents are water, ethanol, polyethyleneglycol and dimethylacetamide as well as mixtures in various proportions of these solvents. Water is a particularly preferred solvent.

To adjust the pH within the range of from 2.5 to about 5.0 a physiologically acceptable acid may be added as desired. The acid may be any physiologically acceptable acid, e.g., an inorganic mineral acid such as hydrochloric, hydrobromic, sulfuric, phosphoric, nitric and the like, or an organic acid such as acetic, succinic, tartaric, ascorbic, citric, glutammic, benzoic, methanesulphonic, ethanesulfonic and the like, or also an acidic physiologically acceptable buffer solution, e.g., a chloride buffer, an acetate buffer, a phosphate buffer and the like.

For obtaining pH values from about 5 to about 5.5 the addition of the acid is not, usually, necessary, but only addition of a physiologically acceptable buffer solution, e.g., one of those indicated above, may be required, as desired.

For obtaining pH values from about 5.5 to 6.5 the addition of a physiologically acceptable alkalinizing agent, such as sodium hydroxide, a mono, di- or triethanolamine or the like, or, preferably, a buffer solution such as a phosphate buffer, a TRIS buffer or the like is required.

The preferred range of pH for the ready-to-use solution of the invention is from 2.5 to 5.5, in particular from about 3 to about 5.2, a pH of about 3 and a pH of about 5 being particularly preferred values.

In the solutions of the invention the concentration of the anthracycline glycoside may vary within broad ranges, preferably from 0.1 mg/ml to 100 mg/ml, in particular from 0.1 mg/ml to 50 mg/ml, most preferably from 1 mg/ml to 20 mg/ml.

The preferred ranges of concentration may be slightly different for different anthracycline glycosides. Thus, for example, preferred concentrations for doxorubicin are from about 2 mg/ml to about 50 mg/ml, preferably from 2 mg/ml to 20 mg/ml, particularly appropriate values being 2 mg/ml and 5 mg/ml. Similar concentrations are preferred also for 4'-epi-doxorubicin, 4'-desoxy-doxorubicin and 4'-desoxy-4'-iodo-doxorubicin. Preferred ranges of concentration for daunorubicin and 4-demethoxydaunorubicin are from 0.1 mg/ml to 50 mg/ml, preferably from 1 mg/ml to 20 mg/ml, concentrations of 1 mg/ml and 5 mg/ml being particularly appropriate.

Suitable packaging for the anthracycline glycoside solutions may be all approved containers intended for parenteral use, such as plastic and glass containers, ready-to-use syringes and the like. Preferably the container is a sealed glass container, e.g. a vial or an ampoule.

According to a particularly preferred feature of the invention, there is provided a sterile, pyrogen-free, doxorubicin solution which consists essentially of a physiologically acceptable salt of doxorubicin dissolved in a physiologically acceptable solvent therefor, which has not been reconstituted from a lyophilizate and which has a pH of from 2.5 to 6.5.

In the above indicated preferred feature of the invention the physiologically acceptable salt of doxorubicin may be, e.g. the salt with a mineral inorganic acid such as hydrochloric, hydrobromic, sulfuric, phosphoric, nitric and the like, or the salt with an organic acid such as acetic, succinic, tartaric, ascorbic, citric, glutamic, benzoic, methanesulfonic, ethanesulfonic and the like. The hydrochloride salt is a particularly preferred salt.

For the solution hereabove indicated as a preferred feature of the invention suitable solvents, co-solubilizing agents, tonicity adjustment agents and preservatives may be the same as those previously recited in this specification. Water is a particularly preferred solvent.

Also, the physiologically acceptable acid which may be added to adjust the pH to from 2.5 to about 5, if desired, and the alkanilizing agent which may be added to adjust the pH, if desired, to a value from about 5.5 to 6.5 may be one of those previously specified. When it is desired to adjust the pH of the above said preferred solution to a value of from 2.5 to about 5, hydrochloric acid is an especially preferred acid. Preferred pH values for the above said preferred solutions of the invention are from 2.5 to 5.5, in particular from about 3 to about 5.2, the pH values of 3 and 5 being especially preferred.

Though the concentration of doxorubicin in the above preferred feature may vary within the broad range from 0.1 mg/ml to 100 mg/ml, preferred concentrations are from 2 mg/ml to 50 mg/ml, most preferably from 2 mg/ml to 20 mg/ml: examples of especially preferred concentrations of doxorubicin are 2 mg/ml and 5 mg/ml.

The invention also provides a process for producing a sterile, pyrogen-free anthracycline glycoside solution with a pH of from 2.5 to 6.5, which process comprises dissolving a physiologically acceptable salt of the anthracycline glycoside, which salt is not in the form of a lyophilizate, in a physiologically acceptable solvent therefor; optionally adding a physiologically acceptable acid or buffer to adjust the pH within the said range as desired; and passing the resulting solution through a sterilising filter.

One or more additional components such as co-solubilizing agents, tonicity adjustment agents and preservatives, for instance of the kind previously specified, may be added to the solution prior to passing the solution through the sterilising filter.

With the solutions of the invention it is possible to obtain compositions having a very high concentration of the anthracycline glycoside active substance even at 50 mg/ml and more. This constitutes a great advantage over the presently available lyophilized preparates wherein high concentrations of anthracycline glycoside can only be obtained with difficulty because of solubilization problems encountered in reconstitution, mainly with saline. The presence of the excipient, e.g. lactose, in the lyophilized cake, and its generally high proportion in respect of the active substance, even up to 5 parts of excipient per part of active substance, has a negative effect on solubilization so that difficulties may arise in obtaining dissolution of the lyophilized cake, especially for concentrations of anthracycline glycoside higher than 2 mg/ml.

The solutions of the invention are characterized by a good stability. Solutions in various solvents and with different pH's and concentrations have been found to be stable for long periods at temperatures accepted for the storage of pharmaceutical preparations. This is illustrated in the Examples which follow.

Owing to the well known anti-tumor activity of the anthracycline glycoside active drug substance, the pharmaceutical compositions of the invention are useful for treating tumors in both human and animal hosts. Examples of tumors that can be treated are, for instance, sarcomas, including osteogenic and soft tissue sarcomas, carcinomas, e.g., breast-, lung-, bladder-, thyroid-, prostate- and ovarian carcinoma, lymphomas, including Hodgkin and non Hodgkin lymphomas, neuroblastoma, melanoma, myeloma, Wilms tumor, and leukemias, including acute lymphoblastic leukemia and acute myeloblastic leukemia.

Examples of specific tumours that can be treated are Moloney Sarcoma Virus, Sarcoma 180 Ascites, solid Sarcoma 180, gross transplantable leukemia, L 1210 leukemia and lymphocytic P 388 leukemia.

Thus, according to the invention there is also provided a method of inhibiting the growth of a tumour, in particular one of those indicated above, which comprises administering to a host suffering from said tumour an injectable solution according to the invention containing the active drug substance in an amount sufficient to inhibit the growth of said tumour.

The injectable solutions of the invention are administered by rapid intravenous injection or infusion according to a variety of possible dose schedules. Suitable dose schedule for doxorubicin may be, for example, of 60 to 75 mg of active drug substance per m$^2$ of body surface given as a single rapid infusion and repeated at 21 days; an alternative schedule may be of 30 mg/m$^2$ by intravenous route for 3 days, every 28 days. Suitable dosages for 4'-desoxy-4'-iodo-doxorubicin. Odarubicin, i.e. 4-demethoxy-daunorubicin, may be, e.g., administered intravenously at a single dose of 13-15 mg/m$^2$ every 21 days in the treatment of solid tumours, while in the treatment of leukemias a preferred dose schedule is, e.g., of 10-12 mg/m$^2$ day by intravenous route for 3 days, to be repeated every 14-21 days; similar dosages may be, e.g., followed also for daunorubicin.

The following examples illustrate but do not limit in any way the invention.

With reference to the examples, the stability controls on the ready-to-use solutions were carried out by means of high performance liquid chromatography (HPLC), at the following experimental conditions:

| | |
|---|---|
| Liquid chromatograph | Varian model 5010 |
| Spectrophotometric detector | Knauer model 8700 |
| Integrating recorder | Varian model CDS 401 |
| Injection valve | Rheodyne model 7125 fitted with a 10 mcl sample loop |
| Chromatographic column | Waters μ-Bondapak C18 (length = 300 mm; inner diameter = 3.9 mm; average particle size = 10 mcm) |
| Column temperature | ambient (about 22° C. ± 2° C.) |
| Mobile phase | water:acetonitrile (69:31 v/v) adjusted to pH 2 with phosphoric acid, filtered (sintered glass filter, 1 mcm or finer porosity) and deaerated |
| Mobile phase flow rate | 1.5 ml/min |
| Analytical wavelength | 254 ± 1 nm |
| Integrating recorder sensitivity | 512 |
| Chart speed | 1 cm/min |

At these conditions, the peak of the anthracycline glycoside showed a retention time of about 6 minutes.

The obtained results are reported in the Tables accompanying the examples.

The extrapolation of the analytical data in order to determine the time when the 90% of the initial assay could be expected ($t_{90}$ value) was made following an Arrhenius plot. This procedure of analytical data treatment is well known and widely used and described in the art: see, e.g., Chemical Stability of Pharmaceuticals, Kennet A. Connors, Gordon L. Amidon, Lloyd Kennon, Publ.John Wiley and Sons, New York, N.Y., 1979. The term "teflon" refers to "Teflon TM".

EXAMPLE 1

| Composition | for 80 vials | (for 1 vial) |
|---|---|---|
| Doxorubicin.HCl | 0.8 g | (10 mg) |
| Water for injections q.s. to | 0.4 l | (5 ml) |

Doxorubicin.HCl (0.80 g) was dissolved in 90 percent of the amount of water for injections, de-aerated by nitrogen bubbling. The pH of the solution was not adjusted. Further de-aerated water for injections was then added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 1:

TABLE 1

| INITIAL VALUES | | | | | | | | |
|---|---|---|---|---|---|---|---|---|
| Concentration:1.994 mg/ml | | | | pH = 5.2 | | | | |
| Relative % Assay: 100.0 | | | | | | | | |
| | TEMPERATURE | | | | | | | |
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.992 | 99.9 | 1.917 | 96.1 | 1.768 | 88.7 | 1.493 | 75.0 |
| 2 | | | 1.843 | 92.4 | 1.618 | 81.1 | 1.166 | 58.5 |
| 3 | | | 1.774 | 89.0 | 1.506 | 75.5 | 0.830 | 41.6 |
| 4 | 1.974 | 99.0 | 1.720 | 86.3 | 1.393 | 69.9 | | |
| 12 | 1.980 | 99.3 | | | | | | |

$t_{90}$ (days) extrapolated according to Arrhenius equation:
$t_{90}$ at 4° C. = 815 days
$t_{90}$ at 8° C. = 480 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubincin, as hydrochloride salts, at both 2 mg/ml and 5 mg/ml concentration.

EXAMPLE 2

| Composition | for 80 vials | (for 1 vial) |
|---|---|---|
| Doxorubicin.HCl | 0.8 g | (10 mg) |

| | | |
|---|---|---|
| Hydrochloric acid 0.1 N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 2:

TABLE 2

INITIAL VALUES

Concentration: 1.992 mg/ml    pH = 3.0
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.995 | 100.2 | 1.952 | 98.0 | 1.919 | 96.3 | 1.493 | 75.0 |
| 2 | | | 1.889 | 94.8 | 1.851 | 92.9 | 1.036 | 51.9 |
| 3 | | | 1.876 | 94.2 | 1.565 | 78.6 | 0.730 | 36.7 |
| 4 | 1.979 | 99.4 | 1.808 | 90.8 | 1.393 | 69.9 | | |
| 12 | 1.972 | 99.1 | | | | | | |

$t_{90}$ (days) extrapolated according to Arrhenius equation:
$t_{90}$ at 4° C. = 3970 days
$t_{90}$ at 8° C. = 2000 days Similar stability data can be observed also for analogous solutions containing either doxorubicin hydrochloride at 5 mg/ml concentration, or 4'-epi-doxorubicin, 4'-dosoxy-doxorubicin, 4'-desoxy-4'-iodo-doxorubicin, daunorubicin or 4-methoxy-daunorubicin, as hydrochloride salts, at both 2 mg/ml and 5 mg/ml concentration.

EXAMPLE 3

| Composition | for 80 vials | (for 1 vial) |
|---|---|---|
| Doxorubicin.HCl | 8.0 g | (100 mg) |
| Hydrochloric acid 0.1 N q.s. to | pH = 3 | (pH = 3) |
| Water for injections q.s. to | 0.4 l | (5 ml) |

Doxorubicin.HCl (8.0 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 3:

TABLE 3

INITIAL VALUES

Concentration: 20.06 mg/ml    pH = 2.95
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 20.06 | 100.0 | 19.56 | 97.5 | 17.84 | 88.9 | 12.31 | 61.4 |
| 2 | | | 18.87 | 94.1 | 15.61 | 77.8 | 7.09 | 35.3 |
| 3 | | | 18.24 | 90.9 | 13.41 | 66.8 | 3.13 | 15.6 |
| 4 | 19.91 | 99.2 | 17.51 | 87.3 | 11.07 | 55.2 | | |
| 12 | 19.80 | 98.7 | | | | | | |

$t_{90}$ (days) extrapolated according to Arrhenius equation:
$t_{90}$ at 4° C. = 3700 days
$t_{90}$ at 8° C. = 1780 days Similar stability data can be observed for analogous solutions containing 4'-epi-doxorubicin or 4'-desoxy-doxorubicin, as hydrochloride salts, at the same 20 mg/ml concentration.

Example 4

| Composition | for 80 vials | (for 1 vial) |
|---|---|---|
| Doxorubicin.HCl | 0.80 g | (10.0 mg) |
| Polyvinylpyrrolidone | 20.00 g | (250.0 mg) |
| Water for injections q.s. to | 0.40 l | (5.0 ml) |

Doxorubicin.HCl (0.80 g) was dissolved in 90 percent of the amount of water for injections, de-aerated by nitrogen bubbling. The pH of the solution was not adjusted. Polyvinylpyrrolidone was added and dissolved under stirring and nitrogen bubbling. Further de-aerated water for injections was then added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 4:

TABLE 4

INITIAL VALUES
Concentration: 1.986 mg/ml   pH = 4.6
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.984 | 99.9 | 1.928 | 97.1 | 1.797 | 90.5 | 1.605 | 80.8 |
| 2 | | | 1.847 | 93.0 | 1.616 | 81.4 | 1.293 | 65.1 |
| 3 | | | 1.828 | 92.0 | 1.527 | 76.9 | 1.018 | 51.3 |
| 4 | 1.928 | 97.1 | 1.797 | 90.5 | 1.403 | 70.7 | | |
| 8 | 1.989 | 100.1 | | | | | | |

$t_{90}$ (days) extrapolated according to Arrhenius equation:
$t_{90}$ at 4° C. = 1460 days
$t_{90}$ at 8° C. = 835 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-methoxy-daunorubicin, as hydrochloride salts, at both 2 mg/ml and 5 mg/ml concentration.

EXAMPLE 5

| Composition | for 80 vials | (for 1 vial) |
|---|---|---|
| Doxorubicin.HCl | 0.800 g | (10.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Doxorubicin.HCl (0.800 g) was dissolved in 90 percent of the amount of water for injections, de-aerated by nitrogen bubbling. N,N-dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.400 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks o weeks (45° C. and 35° C.) and 8 weeks (4° C.). (55° C.), 4 weeks (45° C. and 35° C.) and 8 weeks (4° C.).

The stability data obtained, using high performance liquid chromatography (HPLC) for the determination of potency, are reported in the following Table 5:

TABLE 5

INITIAL VALUES
Concentration: 2.000 mg/ml
Relative % Assay: 100.0   pH = 3.03

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | | | 1.892 | 94.6 | 1.735 | 86.7 | 1.495 | 74.7 |
| 2 | 1.993 | 99.7 | 1.927 | 96.4 | 1.624 | 81.2 | 1.212 | 60.6 |
| 3 | | | 1.908 | 95.4 | 1.432 | 71.6 | 1.032 | 51.6 |
| 4 | 2.00 | 100.0 | 1.863 | 93.2 | 1.266 | 63.3 | | |

TABLE 5-continued

INITIAL VALUES

Concentration: 2.000 mg/ml
Relative % Assay: 100.0            pH = 3.03

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 8 | 1.960 | 98.0 | | | | | | |

$t_{90}$ (days) extrapolated according to Arrhenius equation:
$t_{90}$ at 4° C. = 4360 days
$t_{90}$ at 8° C. = 2200 days Similar stability data can be observed also for analogous solutions containing either doxorubicin hydrochloride at 5 mg/ml concentration, or 4'-epi-doxorubicin, 4'-desoxydoxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 6

| Composition | for 80 vials | (for 1 vial) |
|---|---|---|
| Doxorubicin.HCl | 0.8 g | (10.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (0.8 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 6;

Similar stability data can be observed also for analogous solutions containing either doxorubicin hydrochloride at 5 mg/ml concentration, or 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 7

| Composition | for 80 vials | (for 1 vial) |
|---|---|---|
| Doxorubicin.HCl | 8.00 g | (100.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (8.00 g) was dissolved in 90 percent of the amount of water for injections, de-aerated by nitrogen bubbling. N,N-dimethylacetamide was added under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45°C. and 35° C.) and 8 weeks (4° C.).

The stability data obtained, using high performance liquid chromatography (HPLC) for the determination of potency, are reported in the following Table 7:

TABLE 6

INITIAL VALUES

Concentration: 1.973 mg/ml
Relative % Assay: 100.0            pH = 2.71

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 2.028 | 102.8 | 1.944 | 98.5 | 1.791 | 90.8 | 1.477 | 74.9 |
| 2 | | | 1.885 | 95.5 | 1.582 | 80.2 | 0.972 | 49.3 |
| 3 | | | 1.840 | 93.2 | 1.402 | 71.0 | 0.632 | 32.0 |
| 4 | 1.913 | 97.0 | 1.853 | 93.9 | 1.273 | 64.5 | | |
| 8 | 1.972 | 99.9 | | | | | | |

$t_{90}$ (days) extrapolated according to Arrhenius equation:
$t_{90}$ at 4° C. = 5560 days
$t_{90}$ at 8° C. = 2670 days

TABLE 7

INITIAL VALUES
Concentration: 19.32 mg/ml
Relative % Assay: 100.0      pH = 2.96

TEMPERATURE

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 20.1 | 103.5 | 19.14 | 99.1 | 17.34 | 89.8 | 15.57 | 80.6 |
| 2 |  |  | 19.20 | 99.4 | 15.77 | 81.6 | 12.94 | 67.0 |
| 3 |  |  | 18.06 | 93.5 | 14.85 | 76.9 | 11.61 | 60.1 |
| 4 | 20.03 | 103.7 | 17.81 | 92.2 | 13.78 | 71.3 |  |  |
| 8 | 19.99 | 103.5 |  |  |  |  |  |  |

$t_{90}$ (days) extrapolated according to Arrhenius equation:
$t_{90}$ at 4° C. = 1310 days
$t_{90}$ at 8° C. = 770 days Similar stability data can be observed for analogous solutions containing 4'-epi-doxorubicin or 4'-desoxy-doxorubicin, as hydrochloride salts, at the same 20 mg/ml concentration.

EXAMPLE 8

| Composition | for 80 vials | (for 1 vial) |
|---|---|---|
| Doxorubicin.HCl | 0.80 g | (10.0 mg) |
| Ethanol | 0.12 l | (1.5 ml) |
| Hydrochloric acid 0.1 N q.s. to | pH = 3 | (pH = 3) |
| Water for injections q.s. to | 0.40 l | (5.0 ml) |

Doxorubicin.HCl (0.80g) was dissolved in 90 percent of the amount of water for injections, de-aerated by nitrogen bubbling. Ethanol was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and at 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 8.

Similar stability data can be observed also for analogous solutions containing either doxorubicin hydrochloride at 5 mg/ml concentration, or 4'-epi-doxorubicin, 4'-desoxy-doxorubicin, 4'-iodo-doxorubicin, daunorubicin or 4-methoxy-daunorubicin, as hydrochloride salts, at both 2 mg/ml and 5 mg/ml concentration.

EXAMPLE 9

| Composition | for 80 vials | (for 1 vial) |
|---|---|---|
| Doxorubicin.HCl | 8.000 g | (100.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Doxorubicin.HCl (8.000 g) was dissolved in 90 percent of the amount of water for injections, de-aerated by nitrogen bubbling. N,N-dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.400 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C.

TABLE 8

INITIAL VALUES
Concentration: 1.979 mg/ml
Relative % Assay: 100.0      pH = 3.11

TEMPERATURE

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 2.010 | 101.6 | 1.965 | 99.3 | 1.947 | 98.4 | 1.750 | 88.4 |
| 2 |  |  | 1.957 | 98.9 | 1.910 | 96.5 | 1.645 | 83.1 |
| 3 |  |  | 1.895 | 95.8 | 1.737 | 87.8 | 1.356 | 68.5 |
| 4 | 1.927 | 97.3 | 1.818 | 91.9 | 1.678 | 84.8 |  |  |
| 12 | 1.939 | 97.9 |  |  |  |  |  |  |

$t_{90}$ (days) extrapolated according to Arrhenius equation:
$t_{90}$ at 4° C. = 1270 days
$t_{90}$ at 8° C. = 780 days and 35° C. (accelerated stability controls) and at 4 ° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 9

TABLE 9

INITIAL VALUES
Concentration: 20.07 mg/ml
Relative % Assay: 100.0   pH = 2.99

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | | | 19.14 | 95.4 | 17.81 | 88.7 | 14.84 | 73.9 |
| 2 | 19.97 | 99.5 | 19.07 | 95.0 | 16.27 | 81.1 | 12.36 | 61.6 |
| 3 | | | 18.08 | 90.1 | 14.62 | 72.9 | 10.04 | 50.0 |
| 4 | 20.06 | 99.9 | 18.03 | 89.8 | 13.20 | 65.8 | | |
| 8 | 19.69 | 98.1 | | | | | | |

$t_{90}$ (days) extrapolated according to Arrhenius equation:
$t_{90}$ at 4° C. = 846 days
$t_{90}$ at 8° C. = 505 days and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the folllowing Table 10:

TABLE 10

INITIAL VALUES
Concentration: 19.57 mg/ml   pH = 2.62
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 19.54 | 99.9 | 19.11 | 97.6 | 16.88 | 86.2 | 12.48 | 63.8 |
| 2 | | | 18.43 | 94.2 | 14.13 | 72.2 | 6.00 | 30.7 |
| 3 | | | 18.02 | 92.1 | 11.57 | 59.1 | 2.61 | 13.3 |
| 4 | 19.58 | 100.1 | 17.36 | 88.7 | 9.23 | 47.2 | | |
| 8 | 19.34 | 98.8 | | | | | | |

$t_{90}$ (days) extrapolated according to Arrhenius equation:
$t_{90}$ at 4° C. = 2540 days
$t_{90}$ at 8° C. = 1290 days Similar stability data can be observed for analogous solutions containing 4'-epi-doxorubicin or 4'-desoxy-doxorubicin, as hydrochloride salts, at the same 20 mg/ml concentration.

EXAMPLE 10

| Composition | for 80 vials | (for 1 vial) |
|---|---|---|
| Doxorubicin.HCl | 8.0 g | (100.0 mg) |
| Polyvinylpyrrolidone | 20.0 g | (250.0 mg) |
| Hydrochloric acid 0.1 N q.s. to | pH = 3 | (pH = 3) |
| Water for injections q.s. to | 0.4 l | (5.0 ml) |

Doxorubicin.HCl (8.0 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22 μ microporous membrane under nitrogen pressure Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C.

Similar stability data can be observed for analogous solutions containing 4'-epi-doxorubicin or 4'-desoxy-doxorubicin, as hydrochloride salts, at the same 20 mg/ml concentration.

EXAMPLE 11

| Composition | for 80 vials | (for 1 vial) |
|---|---|---|
| Doxorubicin.HCl | 0.80 g | (10.0 mg) |
| N,N-Dimethylacetamide | 0.12 l | (1.5 ml) |
| Hydrochloric acid 0.1 N q.s. to | pH = 3 | (pH = 3) |
| Water for injections q.s. to | 0.40 l | (5.0 ml) |

Doxorubicin.HCl (0.80 g) was dissolved in 90% of the amount of water for injections, de-aerated by nitrogen bubbling. N,N-Dimethylacetamide was added under stirring and nitrogen bubbling. Hydrochloric acid 0.1N was then added dropwise to adjust the pH of the solution to 3. De-aerated water for injections was finally added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 11:

TABLE 11

INITIAL VALUES
Concentration: 1.826 mg/ml    pH = 3.14
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 1.830 | 100.2 | 1.812 | 99.2 | 1.784 | 97.7 | 1.605 | 87.9 |
| 2 | 1.818 | 99.6 | 1.781 | 97.5 | 1.554 | 85.1 | 1.292 | 70.8 |
| 3 | | | 1.743 | 95.4 | 1.409 | 77.2 | 1.018 | 55.7 |
| 4 | 1.823 | 99.8 | 1.734 | 95.0 | 1.369 | 75.0 | | |
| 8 | 1.792 | 98.2 | | | | | | |

$t_{90}$ (days) extrapolated according to Arrhenius equation:
$t_{90}$ at 4° C. = 5815 days
$t_{90}$ at 8° C. = 2920 days Similar stability data can be observed also for analogous solutions containing either doxorubicin hydrochloride at 5 mg/ml concentration, or 4'-epi-doxorubicin, 4'-desoxy-doxorubicin, 4'-epi-desoxy-4'-iodo-doxorubicin, daunorubicin or 4-demethoxy-daunorubicin, as hydrochloride salts, at both 2 mg/ml and 5 mg/ml concentration.

EXAMPLE 12

| Composition | for 80 vials | (for 1 vial) |
|---|---|---|
| Doxorubicin.HCl | 0.80 g | (10.0 mg) |
| Propylene glycol | 0.12 l | (1.5 ml) |
| Hydrochloric acid 0.1 N q.s. to | pH = 3 | (pH = 3) |
| Water for injections q.s. to | 0.40 l | (5.0 ml) |

Doxorubicin.HCl (0.80 g) was dissolved in 90% of the amount of water for injections de-aerated by nitrogen bubbling. Propylene glycol was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C. and 35° C.) and 4 weeks (4° C.).

The stability data obtained, using high performance liquid chromatography (HPLC) for the determination of potency, are reported in the following Table 12:

TABLE 12

INITIAL VALUES
Concentration: 1.982 mg/ml    pH = 3.11
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 1.972 | 99.5 | 1.934 | 97.6 | 1.889 | 95.3 | 1.705 | 86.0 |
| 2 | | | 1.952 | 98.5 | 1.795 | 90.6 | 1.483 | 74.8 |
| 3 | | | 1.935 | 97.6 | 1.699 | 85.7 | 1.153 | 58.2 |
| 4 | 2.056 | 103.7 | 1.788 | 90.2 | 1.460 | 73.7 | | |

$t_{90}$ (days) extrapolated according to Arrhenius equation:
$t_{90}$ at 4° C. = 1794 days
$t_{90}$ at 8° C. = 1025 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml 5 mg/ml concentration.

EXAMPLE 13

| Composition | for 80 vials | (for 1 vial) |
|---|---|---|
| Doxorubicin.HCl | 0.80 g | (10.0 mg) |
| Polyethylene glycol 400 | 0.12 l | (1.5 ml) |
| Hydrochloric acid 0.1 N q.s. to | pH = 3 | (pH = 3) |
| Water for injections q.s. to | 0.40 l | (5.0 ml) |

Doxorubicin.HCl (0.80 g) was dissolved in 90% of the amount of water for injections, de-aerated by nitrogen bubbling. Polyethylene glycol 400 was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22 μ microporous membrane under nitrogen pressure Volumes of 5 ml of the solution were distributed into type I-colourless glass vials having 5/7 ml capacity The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks. (55° C.), 4 weeks (45° C. and 35 ° C.) and 4 weeks (4° C.).

The stability data obtained, using high performance liquid chromatography (HPLC) for the determination of potency, are reported in the following Table 13:

TABLE 13

INITIAL VALUES
Concentration: 1.907 mg/ml     pH = 3.07
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 1.871 | 98.1 | 1.797 | 94.2 | 1.668 | 87.5 | 1.484 | 77.8 |
| 2 | | | 1.710 | 89.7 | 1.608 | 84.3 | 1.237 | 64.9 |
| 3 | | | 1.739 | 91.2 | 1.551 | 81.3 | 1.007 | 52.8 |
| 4 | 1.873 | 98.2 | 1.693 | 88.8 | 1.453 | 76.2 | | |

$t_{90}$ (days) extrapolated according to Arrhenius equation:
$t_{90}$ at 4° C. = 1130 days
$t_{90}$ at 8° C. = 680 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 14

| Composition | for 80 vials | (for 1 vial) |
|---|---|---|
| Doxorubicin.HCl | 0.8 g | (10 mg) |
| Hydrochloric acid 0.1 N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 4° C. and 8° C. for up to 6 months.

The stability data obtained, using high performance liquid chromatography (HPLC) for the determination of potency, are reported in the following Table 14:

TABLE 14

INITIAL VALUES
Concentration: 2.039 mg/ml     pH = 3.06
Relative % Assay: 100.0

| TIME (months) | TEMPERATURE | | | |
|---|---|---|---|---|
| | 4° C. | | 8° C. | |
| | Conc. mg/ml | Rel. % Assay | Conc. mg/ml | Rel. % Assay |
| 1 | 1.983 | 97.3 | 1.959 | 96.1 |
| 3 | 1.984 | 97.3 | 1.983 | 97.3 |
| 6 | 2.012 | 98.7 | 2.002 | 98.2 |

At the same conditions, similar stability data can be generally observed also for the other solutions mentioned in the preceeding examples.

We claim:

1. A sealed glass container containing therein a stable, intravenously injectable, sterile, pyrogen-free doxorubicin anti-tumor composition in a solution which consists essentially of doxorubicin hydrochloride dissolved in a physiologically acceptable solvent therefor, wherein said solution has not been reconstituted from a lyophilizate, and wherein said solution has a pH adjusted to 2.7114 3.14 with hydrochloric acid, and a concentration of said doxorubicin of from 0.01 to 100 mg/ml.

2. A sealed glass container containing therein a solution according to claim 1 wherein the physiologically acceptable solvent for doxorubicin is chosen from the group consisting of water, ethanol, polyethyleneglycol, dimethylacetamide and mixtures thereof.

3. A sealed glass container containing therein a solution according to claim 2 wherein the physiologically acceptable solvent is water.

4. A sealed glass container containing therein a solution according to claim 1 wherein the concentration of doxorubicin is from 2 mg/ml to 50 mg/ml.

5. A sealed glass container containing therein a solution according to claim 4 wherein the concentration of doxorubicin is from 2 mg/ml to 20 mg/ml.

6. A sealed glass container containing therein a solution according to claim 5 wherein the concentration of doxorubicin is from 2 mg/ml or 5 mg/ml.

* * * * *

UNITED STATES PATENT AND TRADEMARK OFFICE
CERTIFICATE OF CORRECTION

PATENT NO. : 4,946,831
DATED : August 7, 1990
INVENTOR(S) : Gaetano Gatti et al.

It is certified that error appears in the above-identified patent and that said Letters Patent is hereby corrected as shown below:

COLUMN 20
In Claim 1, line 8, "2.7114 3.14" should be --2.71 - 3.14--.

COLUMN 20
In Claim 1, line 9, "0.01 to 100 mg/ml" should read --0.1 to 100 mg/ml--

COLUMN 20
In Claim 6, last line, "is from 2 mg/ml or 5 mg/ml" should be --is 2 mg/ml or 5 mg/ml--.

Signed and Sealed this

Eighteenth Day of February, 1992

Attest:

HARRY F. MANBECK, JR.

Attesting Officer

Commissioner of Patents and Trademarks